United States Patent [19]

Barone

[11] 4,251,390
[45] Feb. 17, 1981

[54] PARTIAL OXIDATION CATALYST
[75] Inventor: Bruno J. Barone, Houston, Tex.
[73] Assignee: Denka Chemical Corporation, Houston, Tex.
[21] Appl. No.: 47,323
[22] Filed: Jun. 11, 1979
[51] Int. Cl.³ .......................... B01J 27/14; B01J 31/02
[52] U.S. Cl. .................................... 252/435; 252/428; 252/429 R
[58] Field of Search .................... 252/428, 429 R, 435
[56] References Cited
U.S. PATENT DOCUMENTS

| | | | |
|---|---|---|---|
| 3,156,706 | 11/1964 | Kerr | 252/435 X |
| 3,255,211 | 6/1966 | Kerr | 260/346.75 |
| 3,985,775 | 10/1976 | Harrison | 252/435 X |
| 4,016,105 | 4/1977 | Kerr | 252/435 X |
| 4,017,521 | 4/1977 | Schneider | 260/346.75 |
| 4,043,943 | 8/1977 | Schneider | 252/435 X |
| 4,062,873 | 12/1977 | Harrison | 252/435 X |
| 4,151,116 | 4/1979 | McDermott | 252/435 |

Primary Examiner—Delbert F. Gantz
Assistant Examiner—William G. Wright
Attorney, Agent, or Firm—Kenneth H. Johnson

[57] ABSTRACT

An improvement in the oxidation catalyst used for the partial oxidation of n-butane and containing vanadium and phosphorus mixed oxides which comprises adding a zinc compound in an amount of from about 0.15 to 0.001/1 Zn/V to the catalyst during the digestion of the reduced vanadium component by concentrated phosphoric acid. The addition of zinc produces a catalyst which is more easily activated and which is very stable to heat upset of the reaction system. Small amounts of lithium and silicon compounds also have additional desirable catalytic effects without diminution of the zinc compound benefit.

20 Claims, No Drawings

PARTIAL OXIDATION CATALYST

BACKGROUND OF THE INVENTION

The present invention relates to an improved catalyst for use in the partial oxidation of hydrocarbons to prepare dicarboxylic acids and anhydrides. More particularly, the parent invention relates to an improved method of preparing phosphorus-vanadium mixed oxide catalyst. The improved method also produces a superior catalyst which is also the subject matter of the present invention.

Basically, all of the methods and oxidation catalysts for this use seek to obtain vanadium in a valence state of less than +5. One method of achieving this is to begin with vanadium in less than the +5 valence state. Another method and that used most widely in the art is to start with vanadium in the +5 state and reduce the valency to less than +5. This invention relates to the latter method.

Usually the reduced vanadium has been obtained by reducing $V_2O_5$ in a solution with HCl to obtain vanadyl chloride. A typical catalyst preparation may involve dissolving the vanadium, phosphorus, and other components in a common solvent, such as hot hydrochloric acid and thereafter depositing the solution onto a carrier. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid, which solvent functions not only to form a solvent for the reaction, but also to reduce the valence of the vanadium compound to a valence of less than 5. For example, a vanadium compound, a copper compound, a tellurium compound, phosphorus compound and alkali metal compound may be dissolved in any order in a suitable reducing solvent and the formation of the complex allowed to take place. Preferably, the vanadium compound is first dissolved in the solvent and thereafter the phosphorus, copper, tellurium and other metal compounds, if any, are added. The reaction to form the complex may be accelerated by the application of heat. The deep blue color of the solution shows the vanadium has an average valence of less than 5. The complex formed is then, without a precipitation step, deposited as a solution onto a carrier and dried. In this procedure, the vanadium has an average valence of less than plus 5, such as about plus 4, at the time it is deposited onto the carrier. Generally, the average valence of the vanadium will be between about plus 2.5 and 4.6 at the time of deposition onto the carrier.

In another method the catalyst is prepared by precipitating the metal compounds, either with or without a carrier, from a colloidal dispersion of the ingredients in an inert liquid. In some instances the catalyst may be deposited as molten metal compounds onto a carrier; however, care must be taken not to vaporize off any of the ingredients such as phosphorus. The catalysts have also been prepared by heating and mixing anhydrous forms of phosphorus acids with vanadium compounds, copper compounds, Me compounds, and the alk-metal compound. The catalysts may be used as either fluid bed or fixed bed catalysts. In any of the methods of preparation, heat may be applied to accelerate the formation of the complex.

A very old and traditional method of obtaining vanadyl chloride as disclosed by Koppel et al, Zeit. anorg. Chem, 45, p. 346–351, 1905 is the reduction of $V_2O_5$ in alcoholic HCl solution. This method has been recommended for the preparation of the phosphorus-vanadium oxidation catalyst for example, by Kerr in U.S. Pat. No. 3,255,211 where the solvent also serves as the reducing agent. Subsequently, U.S. Pat. No. 4,043,943 employed this method of reducing vanadium to prepare the basic phosphorus-vanadium catalyst, however, catalyst produced in this manner are known to require a very specific activation procedure in order to be useful as catalyst, as described for example, in U.S. Pat. No. 4,017,521.

It is a feature of the present invention that the addition of a specific modifier to the phosphorus vanadium mixed oxide catalyst abrogates requirement for the specific activation of the catalyst. It is a further feature of the present invention that the mixed oxide catalyst containing the specific modifier of the present invention is activated by less rigid procedures generally employed for the catalyst prepared by other methods. It is a further feature of the present invention that the modifier containing catalyst of the present invention are extremely stable and give high yields of anhydride for long periods of time.

SUMMARY OF THE INVENTION

The present invention lies in an improvement in the phosphorus-vanadium mixed oxide oxidation catalyst produced by the process comprising reducing vanadium in the +5 valence state in a substantially anhydrous organic medium to a valence of less than +5 and digesting said reduced vanadium in concentrated phosphoric acid wherein the improvement comprises including a promoter containing a zinc compound in the mole ratio of Zn/V in the ranges of 0.15 to 0.001/1 in said catalyst during said digesting thereby obtaining a more easily activated catalyst having superior resistance to deactivation by impurities and excessive heat during use.

In addition to a zinc compound, a small amount of a lithium compound may be in the promotor to enhance selectivity by moderation of the hot spot in the partial oxidation, of n-butane to produce maleic anhydride, e.g., 0.001 to 0.15/1 mole ratio of Li/V. Also small amounts of silicon compound, 0.001 to 0.3 mole ratio Si/V may be added with some moderation in various aspects of performance while retaining the basic improvement.

It should be appreciated that the addition of other components to the catalyst as widely shown in the art is acceptable so long as the basic improvements are not lost as a result thereof.

PREFERRED EMBODIMENTS

More specifically, the improved catalyst is that produced from an alcoholic HCl solution reduction of vanadium pentoxide wherein the organic solvent is an alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It has been found that the reduction temperature should be maintained at no greater than 60° C. and preferably less than 55° C. Optimumly active catalysts are the result when the reduction is carried out at temperatures in the range of about 35° to 55° C., preferably 40° to 55° C.

To obtain the mixed oxides of vanadium and phosphorus, phosphoric acid of approximately 99% $H_3PO_4$ (98 to 101%) is added, for example, prepared from 85 $H_3PO_4$ and $P_2O_5$ or commercial grades of 105 and 115% phosphoric acid diluted with 85% $H_3PO_4$ and the vanadium compound digested which is discerned by a change in the color of the solution to a dark blue green. The alcohol is then stripped off to obtain the dried catalyst.

The digestion of the vanadium compound in the phosphoric acid is normally conducted at reflux until the color change indicated the completed digestion. However, about one hour under these conditions appears to produce the best catalyst. Alternately, equally good catalysts were obtained without reflux digestion by a slow boil up for about 1 to 2 hours with continuous removal of the alcohol, at which time the temperature was increased and the stripping intensified as in a normal alcohol recovery operation.

The alcohol stripping should be conducted to avoid the formation of a crust in the stripper and to produce a flowable slurry. Catalysts prepared from a procedure where a crust has formed have been found to be less active.

The final removal of alcohol is carried out under reduced pressure in an oven generally at temperatures in the range of 110° to 170° C., hence lower temperatures and less rigorous conditions are employed than in the stripping.

It was found that the roasting of the recovered dried catalyst in a flue gas oven for 3 hours at 260° C. produced a more active catalyst than a conventional calcination at 325° C. in a muffle furnace for 1¼ hours. Any activation which will provide comparable conditions can be used, however, the experienced practitioner will evaluate the various combinations to optimize the resultant catalyst performance. Generally calcination or roasting will be at a temperature in the range of 200° to 350° C. for a sufficient period to improve the catalytic properties of the composition.

The temperatures employed are relatively low hence the term calcination may not be appropriate. In any event, heating the composition under these temperature conditions has been found beneficial.

The organic solvent is preferably a primary or secondary alcohol such as methanol, ethanol, 1-proponal, 2-propanol, 1-butanol, 2-butanol, 2-methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylolpropane, diethylene glycol and triethylene glycol. The alcohol is also a mild reducing agent for the vanadium +5 compound.

It has been found that lower ratios of zinc/vanadium produce the most active catalyst and compositions containing Zn/V mole ratio in the range of 0.01 to 0.07 are preferred.

The phosphorus is generally present in these catalysts as well as those of the prior art in the mole ratio of P/V 0.09–1.3/1. Optimum ratios P/V are found to be below 1.22/1 and above 1.0/1.

The point at which the zinc component, lithium component and/or silicon component or other beneficial additives are added is not critical so long as they are present prior to formation of the solid catalyst precipitate. This is conveniently done along with the phosphoric acid addition, thereby assuring the intimate mixing of the catalyst components.

The modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, lithium orthorphosphate, tetra ethyl ortho silicate, silicon tetra chloride, or other organo silones.

The resultant catalyst complex is characterized as a mixed oxide, however, the structure of the complex has not been determined but may be conveniently represented by a formula such as

$$V\ P_aZn_bSi_cLi_dO_x$$

where a is 0.90 to 1.3, b is 0.005 to 0.2, c is 0 to 0.3 and d is 0 to 0.15. This representation is not an empirical formula and has no significance other than representing the atom ratio of the components of the catalyst. The x in fact, has no determinate value and can vary widely depending on the combinations within the complex. That there is oxygen present is known, and the $O_x$ is representative of this.

The catalyst may be employed as pellets, disc, flakes, waffers, or any other convenient shape which will facilitate its use in the tubular reactors employed for this type of vapor phase reaction. The material can be deposited on a carrier, however, when the feed to the reaction is an alkane such as n-butane for the production of maleic anhydride, this is not a desirable arrangement. If the feed was an alkene such as an n-butene the supported cataylst would be a reasonable and economic approach. Since the alkane requires a higher level of activation than the alkenes, it is desirable in the case of a feed of the former to have the catalyst present in an unsupported form in order to provide more sites for activation of the reaction with oxygen. Generally too, the unsupported catalyst will have higher surface area than supported catalysts, which further facilitates activation of the alkanes. The final catalyst particle size for this arrangement is usually about 2½ to about 10 mesh.

Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mol percent hydrocarbons such as n-butane. About 1.0 to about 2.0 mol percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazzard. Lower concentration of $C_4$, less than about one percent, of course, will reduce the total yields obtained at equivalent flow rates and thus are normally economically employed. The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mol percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 415° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

In the following examples two types of reactors were employed. The results of the tests in the two reactors are qualitatively comparable, i.e., an increase in maleic anhydride yield in the smaller equipment will be reflected in the larger equipment, although the absolute numbers may differ.

"A" REACTORS

The "A" reactors are a 4-tube cylindrical brass block (8"O.D.×18") reactor made of alloy 360. The block was heated by two 2500 watt (220 volt) cartridge heaters controlled by means of a 25 amp. thermoelectric proportional controller with automatic reset. Prior to its insulation, the block was tightly wound with a coil of ⅜" copper tubing. This external coil was connected to a manifold containing water and air inlets for cooling of the reactor block. The reactors were made of a 304 stainless steel tube, 1.315" O.D. and 1.049" I.D., 23½" long, containing a centered ⅛" O.D. stainless steel thermocouple well. The lower end of the reactor was packed with a 1" bed of 3 mm pyrex beads. The next 12" of the reactor were packed with catalyst (3/16"×3/16" pellets or 6-12 mesh granules) followed by about a 10" bed of 3 mm pyrex beads. The gas streams are separately metered into a common line entering the top of the reactor. The reaction vapors are passed through two 2000 ml. gas scrubbing bottles containing 800 ml. of water. The vapors from the scrubbers then go through a wet test meter and are vented. The inlet gases are sampled before entering the reactor and after the water scrubbers. The feed is normally 0.5 to 1.8 mol % $C_4$, e.g., n-butane, in air, adjusted to maintain a desired temperature. In addition, operating temperature can be further controlled by dilution of the air with an inert gas.

The inlet gases and water scrubbed outlet gases were analyzed by gas chromatography using the peak area method. Butane, carbon dioxide and any olefins or diolefins present in the gas streams were determined using a ¼" column with a 5' foresection, containing 13 wt. % vacuum pump oil on 35/80 mesh chromosorb, followed by a 40' section containing 26 wt. % of a 70 - 30 volume ratio of propylene carbonate to 2,4-dimethylsulfolane on 35/80 mesh chromosorb. The analysis was conducted at room temperature with hydrogen as the carrier gas (100 ml/minute). Carbon monoxide was analyzed on ¼" column with a 3' foresection of activated carbon followed by a 6' section of 40/50 mesh 5A molecular sieves. This analysis was run at 35° C. with helium as the carrier gas (20 psi).

The water scrub solutions were combined and diluted to 3000 ml. in a volumetric flask. An aliquot of this solution was titrated with 0.1 N sodium hydroxide solution to determine maleic acid (first end point) and weak acids in solution and titrated to determine the carbonyls, using hydroxylamine hydrochloride.

"B" Reactors

The "B" Reactors are 3 to 12 foot tubes varying from ¾ to 1¼ inch inside diameter as specified below. For example, a 3 foot carbon steel tube, ¾ inch inside diameter, "B" reactor employed 300 milliliters of catalyst packed with inert ¼ inch Alundum pellets on top of the catalyst material to a height ⅓ of the height of the catalyst. For each reactor, the catalyst material and inerts above are:

| length diameter | Cat. Size | ml catalyst | inert top packing |
|---|---|---|---|
| 3' × ¾" | ⅛ × ⅛" | 300 | ¼" Alundum* pellets, ⅓ catalyst bed |
| 12' × 1¼" | 3/16 × 3/16" | 1500 | ¼" Alundum pellets |
| 12' × 1" | 5/32 × 5/32" | 950 | 12" at Bottom 6" at Top |

*Fused silica alumina

The reactors were encased in a 7% sodium nitrate −40% sodium nitrate −53% potassium nitrate eutectic mixture constant temperature salt bath. The reactor was slowly warmed to 400° C. (250°-270° C. air passing over catalyst) while passing a gas stream containing 0.5 to 0.7 mol percent n-butane and air over the catalyst beginning at about 280° C. The reactor outlet was maintained at 1 psig. After the reactor had reached 400° C., the catalyst was aged by passing the n-butane—air mixture therethrough for 24 hours. The n-butane—air and temperature was increased to obtain a maximum throughput. The n-butane in the feed is increased to 1.0–1.5 mol percent to obtain 80–90% conversion. The salt bath is operated at a maximum of 425° C. The maximum throughput is achieved in relation to the maximum salt bath temperature and maximum hot spot of about 450° C. The hot spot is determined by a probe through the center of the catalyst bed. The temperature of the salt bath can be adjusted to achieve the desired relationship between the conversion and flow rates of the n-C₄ - air mixture. The flow rate is adjusted to about 85% conversion and the temperature relations given above. Generally, flow rates of about 30 to 75 grams of hydrocarbon feed per liter hour are used. The exit gases were cooled to about 55°-60° C. at about ½ psig. Under these conditions, about 30–50% of the maleic anhydride condenses out of the gas stream. A water scrubber recovery and subsequent dehydration and fractionation were used to recover and purify the remaining maleic-anhydride in the gas stream after condensation. The combined maleic anhydride recovered is purified and recovered at a temperature of about 140°-150° C. overhead and 145° C. bottoms temperature in a fractionator. The purified product had a purity of 99.9+ percent maleic anhydride.

The A reactors provide a relative indication of the results of the salt bath tubs (B reactors) which are intended to reflect a full scale operation.

The method in which the catalyst is prepared is important. Various improvements and perimeters are disclosed above, which when employed in the general procedure will produce superior, stable, long lived catalyst. The following typical catalysts preparative procedures illustrate typical catalyst work up using the information discussed above.

Catalyst Preparation for Example 1

Into a 5 liter glass reactor was charged 1.8 liters of anhydrous isobutyl alcohol and 318 g. of vanadium pentoxide. The reactor was equipped with overhead stirrer, gas inlet, thermowell and a Dean Stark trap with water condensor. Approximately 3.5 lbs. of HCl gas were passed through the stirred suspension at such a rate as to maintain a reaction temperature of about 50° C. To the resulting dark reddish brown solution was added an alcoholic solution of 99.3% phosphoric acid previously prepared by adding 117.2 g. of $P_2O_5$ to 302.58 g. of 85% $H_3PO_4$ until solution was complete and then diluting the acid with 420 ml of anhydrous alcohol. The resulting solution was refluxed for 2.0 hours. Effluent gases were scrubbed with a caustic solution. At the end of the digestion period, the alcohol was stripped until about 1.8 liters were recovered from the dark blue solution. The resulting slurry was dried at 150° C. The dried powder was formed into 3/16"×3/16" tablets.

Catalyst Preparation for Example 21

Into, a 12 liter glass reactor topped with an overhead stirrer, gas inlet tube, thermowell and Dean Stark trap with water condensor, was charged 6.5 liters of anhydrous isobutanol and 1145 g. vanadium pentoxide. Approximately 12.6 lbs. of hydrogen chloride gas was passed into the stirred suspension at such a rate as to maintain a reaction temperature of about 50° C. This rate was increased by the use of a water bath around the reactor. To the resulting dark reddish brown solution was added an alcoholic solution of phosphoric acid previously prepared by adding 586 g. of $P_2O_5$ to 1089.3 g. of 85.5% phosphoric acid in a cooling bath. The acid was diluted with 1.51 liters of anhydrous isobutyl alcohol. 17.17 g. of anhydrous zinc chloride and 1.07 g. of lithium chloride were also added to the reactor. Heat was applied and alcohol removed by distillation over a 4 hour period. The heat was then increased to complete the stripping operation in approximately 3.0 hours. The slurry was dried overnight (16 hours) at 150° C. and then roasted for 3 hours at 260° C. before forming into tablets of the required size.

Isobutyl alcohol was used as the organic solvent in the preparation of each of the catalyst described here.

In the following examples of n-butane partial oxidation to maleic anhydride air in the feed to the reaction is reported as "% air". 100% air=2500⁻¹ GHSV.

The catalyst is conditioned for use by placing the catalyst (pellets, chunks or the like) in the tubular reactor of a fixed bed reactor and carrying out the conditioning. The reactor (B) is heated by the salt bath.

The term "rapid conditioning" means heating the catalyst to a temperature of 380° C. in a stream of air flowing at about 1.5 V/V/min at a temperature increase of 3° C. per minute, maintaining the air flow and temperature for two hours, increasing the temperature to 480° C. at 4° C. per minute at the same air flow while butane was fed at 1.5 mole % concentration where it was held for an additional 16 hours and thereafter adjusted to provide a 90% conversion at air flow of 1000$^{-1}$ hours GHSV and 1.5 mole % butane.

The term "standard conditioning" means a slow bring-up of the catalyst to operating temperature at the rate of 5° to 10° C. per hour achieved by heating the reactor and adjusting the gas flow from 0.5 to 1.0 mole % butane in air at an initial air flow of GHSV of 900$^{-1}$ hours up to 2500$^{-1}$ hours while maintaining a desired conversion level, e.g., about 75 mole %, the procedure requiring in general several days.

In both procedures, the initial temperature of the salt bath is about 250° C. (a point where the salt bath is molten). The rapid conditioning can be obtained in laboratory equipment, however, it can not be obtained in large scale multitube reactors of the type used for commercial production of maleic anhydride, since the rapid conditioning requires a 3° C. per minute increase in the salt bath temperature, which is not possible with the full scale commercial reactors.

The C, S and Y used in reporting reaction results have the following meaning and relationship C(conversion)×S(selectivity)=Y(yield).

The principal draw back to the rapid conditioning which is required to produce the most active unmodified catalyst is that the general nature of the conventional tubular reactors do not accommodate that procedure and the catalyst if used commercially would have to be conditioned prior to loading in the reactor tubes. The loading itself would likely subject the catalyst to weather and potential contamination, hence in situ conditioning is more desirable, which is readily obtained with the standard conditioning procedure which may be used with the present modified catalyst.

EXAMPLES 1-8

The effect of the modifier on the basic PVO catalyst is demonstrated by comparing the basic unmodified catalyst prepared by the anhydrous method and conditioned by several different procedures and a zinc modified catalyst similarly conditioned. The data reported in TABLE I shows that presence of zinc provides an equally active catalyst after less rigorous conditioning. Examples 1, 2 and 3 used the same catalyst, similarly examples 4 and 5 are the same catalyst and examples 6 and 7 are the same catalyst.

TABLE I

| Example | Catalyst | Conditioning | Reactor | Temperature °C. Block | Temperature °C. Hot Spot | Mole % C$_4$ Feed | % Air | Hrs. on Steam | Mole % M.A. C | Mole % M.A. S | Mole % M.A. Y |
|---|---|---|---|---|---|---|---|---|---|---|---|
| 1 | VP$_{1.2}$O$_x$ | Rapid | A | 397 | 463 | 0.762 | 100 | 746 | 79.8 | 55.1 | 44.0 |
| 2 | VP$_{1.2}$O$_x$ | Standard, calcined at 350° C. | A | 416 | 452 | 0.697 | 100 | 455 | 61.7 | 63.1 | 38.9 |
| 3 | VP$_{1.2}$O$_x$ | Standard | A | 416 | 451 | 0.731 | 100 | 455 | 60.5 | 63.2 | 38.2 |
| 4 | VP$_{1.2}$Zn$_{0.1}$O$_x$ | Standard | A | 392 | 451 | 0.879 | 100 | 501 | 69.7 | 64.0 | 44.6 |
| 5 | VP$_{1.2}$Zn$_{0.1}$O$_x$ | Rapid | A | 392 | 406 | 0.847 | 100 | 313 | 25.1 | 72.6 | 18.6 |
| 6 | VP$_{1.2}$Zn$_{0.1}$Li$_{0.01}$O$_x$ | Rapid | A | 395 | 402 | 1.363 | 40 | 243 | 12.0 | 70.9 | 8.5 |
| 7 | VP$_{1.2}$Zn$_{0.1}$Li$_{0.01}$O$_x$ | Standard | A | 400 | 446 | 0.866 | 100 | 601 | 67.9 | 67.2 | 45.7 |
|   |   |   | A | 415 | 470 | 0.809 | 100 | 1129 | 77.4 | 61.9 | 47.9 |
| 8 | VP$_{1.2}$Zn$_{0.1}$Si$_{0.05}$O$_x$ | Standard | A | 386 | 453 | 0.834 | 100 | 612 | 76.0 | 63.2 | 48.0 |

EXAMPLES 9-11

It was found the zinc concentration could be very low and still provide the improvement of a more active catalyst (standard conditioning) than the unmodified catalyst and have an even more desirable performance in oxidations. The tests were carried out in the A reactors over 961 hours. The higher zinc concentration reflected the highest time trend as shown in TABLE II. Standard conditioning was employed for each catalyst.

TABLE II

| Example | Catalyst | Temp., °C. Block | Temp., °C. Hot Spot | Mole % C$_4$Feed | % Air | Hrs. on Stream | Mole % C | Maleic S | Anhydride X |
|---|---|---|---|---|---|---|---|---|---|
| 9 | VP$_{1.2}$Zn$_{0.01}$O$_x$ | 371 | 389 | 0.679 | 55 | 119 | 51.0 | 61.7 | 31.4 |
|   |   | 387 | 456 | 0.783 | 100 | 191 | 72.0 | 56.6 | 40.8 |
|   |   | 392 | 451 | 0.853 | 100 | 312 | 76.6 | 57.8 | 44.2 |
|   |   | 396 | 452 | 0.748 | 100 | 461 | 76.6 | 60.9 | 46.7 |
|   |   | 400 | 458 | 0.794 | 100 | 672 | 74.7 | 59.3 | 44.3 |
|   |   | 399 | 455 | 0.816 | 100 | 961 | 75.4 | 59.7 | 45.0 |
| 10 | VP$_{1.2}$Zn$_{0.04}$ | 371 | 376 | 0.722 | 55 | 119 | 54.7 | 62.8 | 34.4 |
|   |   | 387 | 455 | 0.836 | 100 | 191 | 72.0 | 59.4 | 42.8 |
|   |   | 392 | 446 | 0.792 | 100 | 312 | 76.8 | 60.6 | 46.5 |
|   |   | 396 | 447 | 0.795 | 100 | 461 | 76.9 | 58.6 | 45.0 |
|   |   | 400 | 448 | 0.804 | 100 | 672 | 74.0 | 60.9 | 45.0 |
|   |   | 399 | 453 | 0.786 | 100 | 961 | 71.4 | 62.5 | 44.6 |
| 11 | VP$_{1.2}$Zn$_{0.1}$O$_x$ | 371 | 383 | 0.701 | 55 | 119 | 65.5 | 61.7 | 40.4 |
|   |   | 387 | 453 | 0.813 | 100 | 191 | 73.6 | 58.0 | 42.7 |
|   |   | 392 | 449 | 0.805 | 100 | 312 | 76.7 | 61.0 | 46.8 |
|   |   | 396 | 449 | 0.826 | 100 | 461 | 74.5 | 62.2 | 46.3 |
|   |   | 400 | 448 | 0.797 | 100 | 672 | 66.4 | 62.9 | 41.7 |
|   |   | 399 | 444 | 0.818 | 100 | 961 | 62.0 | 66.7 | 41.3 |

EXAMPLES 12-20

The effects of temperature of the vanadium reduction (TABLE II) and "calcination" of the recovered solid catalyst are discussed above. The conventional approach was a 325° C. "calcination", however, such a relative low temperature may be questioned as to whether it was a true calcination. In any event, it was found that a much lower temperature, e.g., 260° C. in a flue gas oven, i.e., a roasting, produced a better catalyst (TABLE IV). Similarly it was found that moderate reduction temperatures also produced better catalysts. This coupled with the observation during stripping would tend to indicate that processing temperature conditions should be toward the lower end or even less than the art would indicate for the preparative methods. The reactions were carried out in the A reactors.

Table III*

| Example | Reduction Temp. °C. | Temp., °C. Block | Temp., °C. Hot Spot | Mole % C$_4$Feed | % Air | Hrs. on Stream | Mole % M. A. C | Mole % M. A. S | Mole % M. A. X |
|---|---|---|---|---|---|---|---|---|---|
| 12 | 38 | 392 | 434 | 0.823 | 100 | 500 | 64.2 | 60.6 | 38.9 |
| 13 | 38 | 392 | 442 | 0.814 | 100 | 500 | 72.0 | 66.8 | 48.1 |
| 14 | 38 | 392 | 431 | 0.816 | 100 | 500 | 63.1 | 62.2 | 39.3 |
| 15 | 74 | 392 | 419 | 0.781 | 100 | 500 | 46.1 | 61.7 | 28.8 |
| 16 | 108 | 402 | 442 | 0.801 | 100 | 501 | 68.3 | 66.4 | 45.3 |

*$VP_{1.2}Zn_{0.1}O_x$ Standard conditioning

TABLE IV*

| Example | Hours Roasted at 260°C. | Temp., +C. Block | Temp., +C. Hot Spot | Mole % C$_4$ Feed | Hrs. On Air | Stream | Mole % M.A. C | Mole % M.A. S | Mole % M.A. Y |
|---|---|---|---|---|---|---|---|---|---|
| 17 | 1 | 397 | 436 | 0.757 | 100 | 1248 | 62.6 | 71.7 | 44.9 |
| 18 | 2 | 397 | 436 | 0.843 | 100 | 1248 | 58.6 | 70.5 | 41.3 |
| 19 | 3 | 397 | 456 | 0.720 | 100 | 1248 | 74.0 | 65.4 | 48.4 |
| 20 | 3** | 397 | 456 | 0.685 | 100 | 1248 | 71.7 | 64.6 | 46.5 |

*$VP_{1.2}Zn_{0.1}Li_{0.02}O_x$ Standard Conditioning
**Dried 4 hours under vacuum before roasting for 3.0 hours at 260° C.

EXAMPLES 21-26

The larger reactors provide comparable results to the brass block reactors over comparable periods and similar conditions as can be seen in TABLE V. The catalyst were subject to standard conditioning.

EXAMPLE 27

During different evaluations, temperature upsets have subjected the present zinc modified catalyst to very high temperatures, which would have been expected to result in deactivation, however the catalyst activity has returned to the same level, afterwards and in some observation higher levels of activity after the upset. For example, one $VP_{1.2}Zn_{0.1}$ $Li_{0.02}O_x$ in a 1¼"×12' reactor (10¼' bed of 3/16"×3/16" tablets) had a hot spot of 555° C. for 3 hours as a result of equipment failure. Prior to that time, the highest hot spot had been 447° C. at 3028 hours on steam (C, S, Y=76.4, 60.1, 45.9) after the upset at 3054 hours the hot spot was 440° C. (C, S, Y=74.3, 62.9, 46.8). This remarkable temperature stability could hardly be expected, particularly in view of the sensitivity of the catalyst to the temperature conditions of the preparative process.

The invention claimed is:

1. In a phosphorous-vanadium mixed oxide oxidation catalyst mole ratio P/V being 0.90 to 1.3/1 produced by the process comprising reducing vanadium in the +5 valence state in a substantially anhydrous organic medium to a valence of less than +5 and digesting said

TABLE V

| Example | Catalyst | "B" Reactor | Temp. °C. Salt | Temp. °C. Hot Spot | Mole % C$_4$ Feed | % Air | Hrs. On Steam | Mole % M.A. C | Mole % M.A. S | Mole % M.A. Y |
|---|---|---|---|---|---|---|---|---|---|---|
| 21 | $VP_{1.2}Zn_{0.01}$ $Li_{0.005}O_x$ | 1" × 12' 10¼' bed 5/32" × 5/32" Tablets | 396 | 450 | 1.65 | 100 | 1435 | 76.9 | 63.8 | 49.1 |
| 22 | **$VP_{1.15}Zn_{0.04}$ $Li_{0.02}O_x$ | 1"×12' 10¼' bed 5/32" × 5/32" Tablets | 425 | 442 | 1.23 | 80 | 387 | 67.9 | 65.0 | 40.9 |
| 23 | **$VP_{1.15}Zn_{0.04}$ $Li_{0.02}O_x$ | ¾" ×3'* ⅛" × ⅛" Tablets | 425 | 475 | 1.34 | 100 | 147 | 67.3 | 63.0 | 40.5 |
| 24 | **$VP_{1.15}Zn_{0.04}$ $Li_{0.02}O_x$ | ¾" × 3' 18/" × ⅛" Tablets | 420 | 436 | 0.91 | 80 | 430 | 61.3 | 63.1 | 38.7 |
| 25 | $VP_{1.2}Zn_{0.1}$ $Si_{0.05}O_x$ | ¾" ×3' ⅛" × ⅛" Tablets | 396 | 449 | 1.29 | 100 | 1882 | 74.8 | 63.2 | 47.3 |
| 26 | $VP_{1.2}Zn_{0.04}$ $Si_{0.05}O_x$ | ¾" × 3' ⅛" × ⅛" Tablets | 401 | 480 | 1.291 | 100 | 1532 | 78.2 | 56.7 | 44.3 |

*accelerated bring up 300°-425° C. in 24 hours (not "rapid" as defined, but at a faster rate than "standard" conditioning).
**Calcined at 325° C. for 1 ¼ hrs.

reduced vanadium in concentrated phosphoric acid wherein the improvement comprises including a promoter containing a zinc compound in the mole ratio of Zn/V in the range of 0.15 to 0.001/1 in said catalyst during said digesting thereby obtaining a catalyst activated by bringing said catalyst to operating temperature at a rate of 5 to 10° C. per hour.

2. The phosphorus-vanadium mixed oxide oxidation catalyst according to claim 1 wherein the organic medium is an alcohol, vanadium +5 is present in the compound $V_2O_5$ and HCl is present therein as a reducing agent.

3. The phosphorus-vanadium mixed oxide oxidation catalyst according to claim 1 wherein in addition to said zinc compound a lithium compound is added during the digesting in an amount of 0.001 to 0.15/1 Li/V mole ratio.

4. The phosphorous-vanadium mixed oxide oxidation catalyst according to claim 1 wherein in addition to said zinc compound a silicon compound is added during the digesting in an amount of 0.001 to 0.30/1 Si/V mole ratio.

5. The phosphorous-vanadium mixed oxide oxidation catalyst according to claim 2 wherein the temperature during the education is in the range of 35° to 60° C.

6. The phosphorus-vanadium mixed oxide oxidation catalyst according to claim 2 wherein the phosphoric acid has a concentration of about 98 to 101% $H_3PO_4$.

7. The phosphorus-vanadium mixed oxide oxidation catalyst according to claim 5 wherein the temperature during the reduction is in the range of 40° to 55° C.

8. The phosphorous-vanadium mixed oxide oxidation catalyst according to claim 2 wherein said alcohol is a primary or secondary alcohol.

9. A substantially anhydrous process for producing improved phosphorus-vanadium mixed oxide oxidation catalysts comprising:

admixing a +5 valence vanadium compound with an alcohol, contacting said mixture with gaseous HCl until the valence of vanadium is reduced to less than +5 at a temperature in the range of 35° to 60° C., digesting said reduced vanadium in concentrated phosphoric acid of about 98 to 101% $H_3PO_4$, adding a modifier containing a zinc compound in the mole ratio of Zn/V of 0.15 to 0.001/1 during said digesting, stripping said alcohol from said digested mixture to form a slurry of mixed oxides and alcohol, removing the remaining alcohol under reduced pressure at a temperature in the range of 110° to 170° C., recovering a dried mixed oxide composition and heating said dried mixed oxide composition at a temperature in the range of 200° to 300° C. for a sufficient period to improve the catalytic properties of the composition.

10. The process according to claim 9 wherein said alcohol is a primary or secondary alcohol.

11. The process according to claim 9 wherein said zinc compound is selected from acetate, carbonate, chloride, bromide, oxide, hydroxide or phosphate.

12. The process according to claim 8 wherein in addition to said zinc compound a lithium compound is added during the digesting in an amount of 0.001 to 0.15/1 Li/V mole ratio.

13. The process according to claim 9 wherein in addition to said zinc compound is added during the digesting in a amount of 0.001 to 0.30/1 Si/V mole ratio.

14. The phosphorus-vanadium mixed oxide oxidation catalyst according to claim 9 wherein said alcohol is a primary or secondary alcohol selected from methanol, ethanol, 1-propanol, 2-propanol, 1-butanol, 2-butanol, 2-methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylolpropane, diethylene glycol or triethylene glycol.

15. The phosphorus-vanadium mixed oxide oxidation catalyst according to claim 4 wherein said alcohol is 2-methyl-1-propanol.

16. The phosphorus-vanadium mixed oxide oxidation catalyst according to claim 15 wherein said zinc compound is selected from acetate, carbonate, chloride, bromide, oxide, hydroxide or phosphate.

17. The phosphorus-vanadium mixed oxide oxidation catalyst according to claim 15 or 16 said zinc compound is zinc chloride.

18. The process according to claim 10 wherein said primary or secondary alcohol is selected from methanol, ethanol, 1propanol, 2-propanol, 1-butanol, 2-butanol, 2-methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylolpropane diethylene glycol or triethylene glycol.

19. The process according to claim 18 wherein the alcohol is 2-methyl-1-propanol.

20. The process according to claim 19 or 11 wherein said zinc compound is zinc chloride.

* * * * *

UNITED STATES PATENT OFFICE
CERTIFICATE OF CORRECTION

PATENT NO. : 4,251,390

DATED : February 17, 1981

INVENTOR(S) : Bruno J. Barone

It is certified that error appears in the above-identified patent and that said Letters Patent are hereby corrected as shown below:

Column 1, Line 8 reads "the parent" but should read --- the present ---

Column 2, line 26 reads "catalyst" but should read --- catalysts ---

Column 5, Line 13 reads "and thus are normally" but should read --- but thus are not normally ---

Column 8, Line 4 reads "salt bath tubs" but should read --- salt bath tubes ---

Column 11-12, TABLE III, right hand heading, second line reads "X" but should read --- Y ---

Column 13, Claim 2, line 4 reads "HCl" but should read --- HCl ---

Column 13, claim 5, line 3 reads "education" but should read --- reduction ---

Column 14, claim 12, Line 1 reads "claim 8" but should read --- claim 9 ---

Column 14, claim 13, line 2 reads "compound is added" but should read ---compound a silicon compound is added ---

UNITED STATES PATENT OFFICE
CERTIFICATE OF CORRECTION

PATENT NO. : 4,251,390

DATED : February 17, 1981

INVENTOR(S) : Bruno J. Barone

It is certified that error appears in the above-identified patent and that said Letters Patent are hereby corrected as shown below:

Column 14, claim 14, line 2 reads "claim 9" but should read --- claim 8 ---

Column 14, claim 15, line 2 reads "claim 4" but should read --- claim 14 ---

Column 14, claim 16, line 3 reads "1propanol" but should read --- 1-propanol ---

Signed and Sealed this

Second Day of September 1986

[SEAL]

Attest:

DONALD J. QUIGG

Attesting Officer

Commissioner of Patents and Trademarks